(12) United States Patent  
Weselak et al.

(10) Patent No.: US 7,329,394 B2
(45) Date of Patent: Feb. 12, 2008

(54) HIGH THROUGHPUT INCUBATION DEVICES

(75) Inventors: Mark R. Weselak, San Diego, CA (US); Robert C. Downs, La Jolla, CA (US)

(73) Assignee: IRM LLC, Hamilton (BM)

( * ) Notice: Subject to any disclaimer, the term of this patent is extended or adjusted under 35 U.S.C. 154(b) by 782 days.

(21) Appl. No.: 10/200,021

(22) Filed: Jul. 18, 2002

(65) Prior Publication Data

US 2003/0031602 A1 Feb. 13, 2003

Related U.S. Application Data

(60) Provisional application No. 60/306,481, filed on Jul. 18, 2001.

(51) Int. Cl.
*B01L 9/00* (2006.01)

(52) U.S. Cl. ............... 422/104; 422/99; 221/150 R; 221/150 A; 221/150 HC; 312/42; 312/50

(58) Field of Classification Search ............ 422/62, 422/67, 99, 102, 104; 436/43, 46, 50, 174, 436/176; 221/9, 135, 150 R, 150 A, 150 HC, 221/277; 435/286.1, 307.1, 309.1; 312/35, 312/42, 50
See application file for complete search history.

(56) References Cited

U.S. PATENT DOCUMENTS

| | | | |
|---|---|---|---|
| 4,676,951 A | | 6/1987 | Armes et al. |
| 4,720,463 A | * | 1/1988 | Farber et al. ............ 435/286.5 |
| 5,149,654 A | * | 9/1992 | Gross et al. ............. 435/303.1 |
| 5,266,766 A | * | 11/1993 | Hecox ........................ 219/680 |
| 5,313,393 A | * | 5/1994 | Varley et al. ................. 705/28 |
| 5,470,744 A | | 11/1995 | Astle |
| 5,501,364 A | * | 3/1996 | Cooper ........................ 221/12 |
| 5,525,512 A | | 6/1996 | Pieler et al. |
| 5,579,952 A | * | 12/1996 | Fiedler et al. .......... 221/150 A |
| 5,727,654 A | * | 3/1998 | Roessner et al. ............. 186/40 |
| 5,730,316 A | * | 3/1998 | Falk ........................... 221/122 |
| 5,735,587 A | | 4/1998 | Malin et al. |
| 5,955,373 A | * | 9/1999 | Hutchins et al. .............. 436/48 |
| 6,096,272 A | | 8/2000 | Clark et al. |
| 6,099,230 A | * | 8/2000 | Hitch .................... 414/331.02 |
| 6,129,428 A | | 10/2000 | Helwig et al. |
| 6,228,636 B1 | | 5/2001 | Yahiro et al. |
| 6,265,695 B1 | * | 7/2001 | Liebermann ................. 219/385 |
| 6,297,047 B1 | * | 10/2001 | Butts ........................ 435/303.1 |
| 6,475,776 B1 | * | 11/2002 | Higuchi .................... 435/303.3 |
| 6,536,859 B1 | * | 3/2003 | Bathe ........................ 312/305 |
| 6,568,770 B2 | * | 5/2003 | Gonska et al. ............. 312/9.12 |
| 6,752,479 B2 | * | 6/2004 | Ferger et al. ................ 312/350 |

(Continued)

OTHER PUBLICATIONS

"Cell Based Assay System" CRS Robotics web page (2 pages): http://www.crsrobotics.com/web_pdf/Cell_Based_Assay.pdf.

(Continued)

*Primary Examiner*—Jill Warden
*Assistant Examiner*—Dwayne K. Handy
(74) *Attorney, Agent, or Firm*—Timothy L. Smith; Genomics Institute of the Novartis Research Foundation

(57) ABSTRACT

The invention provides an efficiently automated incubation device that reduces the number of powered moving parts in the device and the amount of air transfer between environments that are internal and external to the device.

39 Claims, 11 Drawing Sheets

U.S. PATENT DOCUMENTS

| | | | |
|---|---|---|---|
| 6,881,572 B2 * | 4/2005 | Fitzgerald et al. | 435/303.3 |
| 2004/0115101 A1 * | 6/2004 | Malin | 422/104 |
| 2004/0213651 A1 * | 10/2004 | Malin | 414/331.05 |
| 2004/0256963 A1 * | 12/2004 | Affleck et al. | 312/209 |
| 2005/0084955 A1 * | 4/2005 | Tamaoki et al. | 435/303.1 |

OTHER PUBLICATIONS

"Sagian—Microplate CS Incubator" Beckman Coulter web page: http://www.beckman.com/products/instrument/automatedsolutions/integsystems/sagian_csincubator_inst_dcr.asp.

"Tomtec: Mega-Stor microplate bulk storage" Tomtec web page: http://www.tomtec.com/Pages/Mega-Stor.html.

Astle, Thomas W. (2000) "Lean Screening" JALA, vol. 5, No. 1.

"HTS Solutions—Cytomat" Beckman Coulter web page (4 pages): http://www.beckman.com/resourcecenter/labresources/automatedsolutions/pdf/cytomat6000.pdf.

"This tiny door opens the possibilities for your next big hit", advertisement for Kendro Laboratory Products.

* cited by examiner

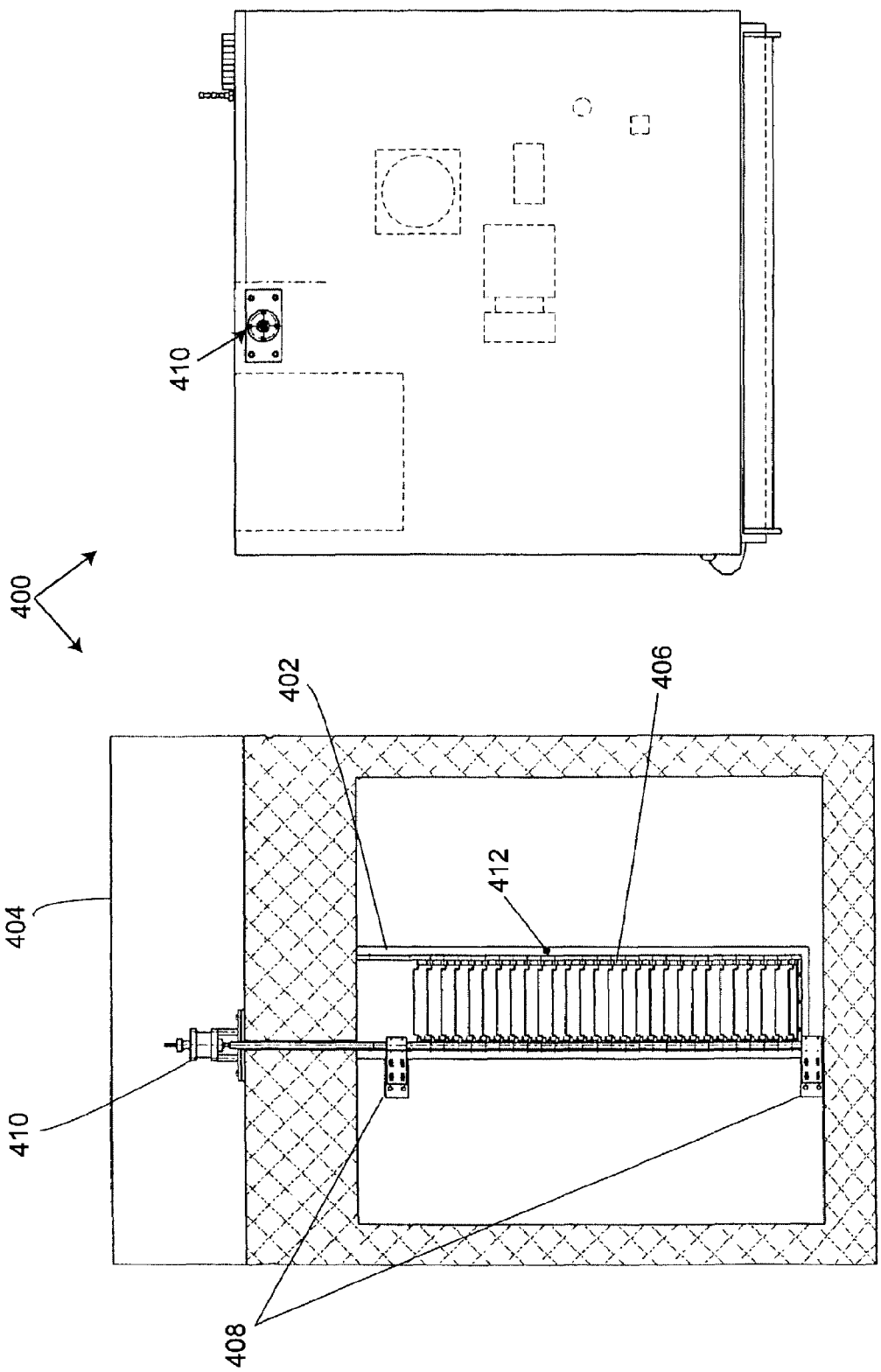

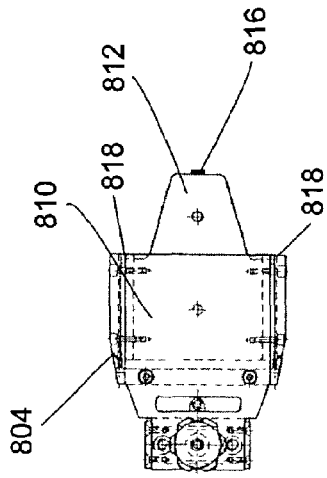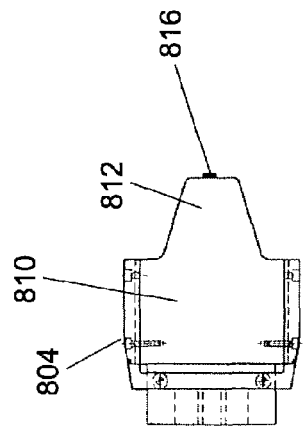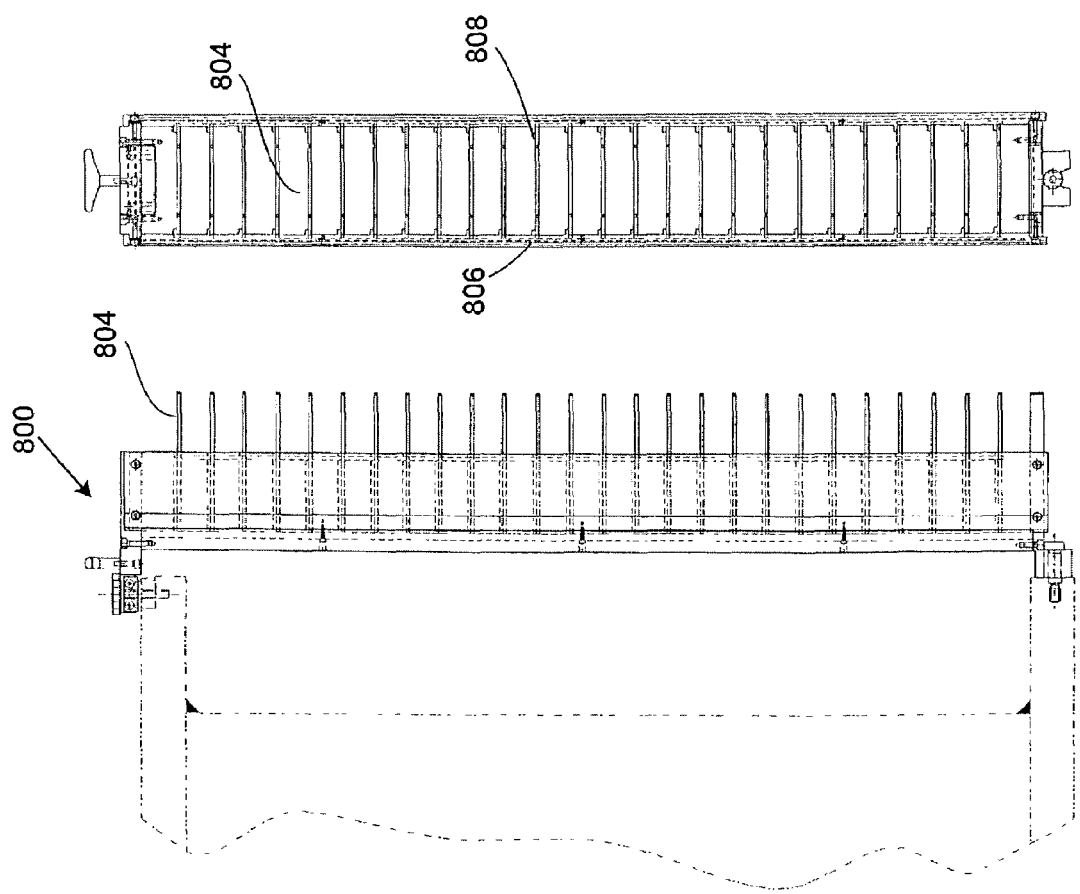

HIGH THROUGHPUT INCUBATION DEVICES

CROSS-REFERENCE TO RELATED APPLICATIONS

This application claims priority to and benefit of U.S. provisional patent application Ser. No. 60/306,481, filed Jul. 18, 2001, which is incorporated herein by reference in its entirety for all purposes.

COPYRIGHT NOTIFICATION

Pursuant to 37 C.F.R. §1.71(e), Applicants note that a portion of this disclosure contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

STATEMENT AS TO RIGHTS TO INVENTIONS MADE UNDER FEDERALLY SPONSORED RESEARCH AND DEVELOPMENT

Not Applicable.

FIELD OF THE INVENTION

This invention relates to laboratory incubators employed to store chemical compounds, cells, mixtures or other materials.

BACKGROUND OF THE INVENTION

Laboratory incubators are used, e.g., to store chemical compounds, cells, mixtures or other materials in a controlled atmospheric environment. A design for an incubator typically maximizes device storage capacity, while minimizing air transfer between the internal and external environments when sample containers are loaded into and unloaded from the device. Incubators in current use either include a single large door or an internal mechanism. Access to large door units requires opening the single large door, which exposes the entire storage area to the uncontrolled external environment. It is difficult to maintain internal stability (e.g., a selected temperature, a desired humidity level, a gas composition, etc.) when opening such large doors, because large volumes of air transfer between the controlled and uncontrolled environments. In contrast, an internal mechanism incubator includes a single small mechanically actuated door or slot through which sample containers are robotically or manually passed from the external environment. A secondary system, e.g., a robot, disposed in the controlled environment of the incubator then moves the container or other labware to its storage location within the device. Although this method reduces air transfer between controlled and uncontrolled environments, the secondary system disposed in the device is required to move objects within the incubator. Furthermore, breaches to the barrier between controlled and uncontrolled environments of these devices also result when repairs to the secondary system are required.

Accordingly, it would be desirable to provide a simplified incubation device that reduces air exchange between internal and external environments. The invention provides this and a variety of additional features that will become apparent upon complete review of the following disclosure.

SUMMARY OF THE INVENTION

In one aspect, the invention relates to an incubation device that includes (a) a housing that includes at least two doors (e.g., between, e.g., two and about 50 or more doors, about four and about 50 or more doors, about three and about 40 or more doors, about three and about 30 or more doors), which doors close an opening disposed through a surface of the housing and (b) a door hold-open mechanism that comprises a member to which is attached a plurality of prongs, wherein the member is positioned such that one prong is adjacent to each of at least two doors in the vertical column of doors. Movement of the door hold-open mechanism in a direction parallel to a longitudinal axis of the vertical column of doors results in a prong contacting any door that is at least partially open, thereby holding open the door that is at least partially open. The incubation device can further include an actuating device that moves the door hold-open mechanism back and forth in the direction parallel to the longitudinal axis of the column of doors. If the doors are hinged at a bottom edge of the door, for example, downward movement of the door hold-open mechanism results in a prong contacting any door that is at least partially open, thereby holding the door open until the door hold-open mechanism is moved in an upward direction, which releases the door. At least one of the doors, and preferably all of the doors in the vertical column of doors, have a restraining mechanism connected thereto that closes the door closed in the absence of an applied opposing force.

The incubation devices can also include a sample container handling apparatus disposed external to the housing, which handling apparatus is capable of moving a sample container through the opening to or from the shelf. In some embodiments, the incubation devices include a controller operably connected to the housing, which controller controls internal housing conditions (e.g., temperature, humidity, gas composition, and/or the like).

The doors of the incubation device of the invention can be arranged in any of a variety of embodiments. In one embodiment, each of the doors in the vertical column is independently accessible by the sample container handling apparatus. The vertical column can be disposed within an access panel. In one aspect, the access panel is hinged to the housing on one side. In another aspect, the access panel is disposed within an additional door in the housing. Optionally, the access panel and/or additional door include(s) a gasket and/or a lock or latch to maintain the access panel and/or additional door in a closed or open position. In another embodiment, the incubation device includes an additional door, e.g., a maintenance door, which optionally includes a gasket and a lock or latch.

The sample container handling apparatus can open a door on the housing. Typically, the sample container handling apparatus includes a robotic armature. In one embodiment, the sample handling apparatus includes a gripper, which grasps a sample container for movement in or out of the incubation device. Sample containers of the invention include a plate, a sample plate, a micro-well plate, a reaction block, a reaction block carrier, a sample holder, a petri dish, a test tube, a test tube rack, a vial, a crucible, a reaction vessel, a reaction flask, a tray or the like.

The incubation devices of the invention also optionally include a logic device (e.g., including a computer) operably connected at least to the sample container handling apparatus, which logic device includes one or more logic instructions that direct movement of the sample container handling apparatus.

The incubation devices of the invention also typically include a restraining mechanism that restrains a door aligned with the shelf to prevent the door from closing when the sample container handling apparatus moves the sample container through the opening to or from the shelf. The restraining mechanism is optionally controlled by an actuator that is located external to the housing. Further, a door generally includes an actuation mechanism operably connected thereto that closes the door in the absence of a sufficient applied opposing force. The actuation mechanism is typically self-actuating (e.g., a spring or the like).

The incubation devices can also include at least one movable shelf disposed within the housing, which shelf is capable of aligning with the opening. Individual shelves of the incubation device typically include components to aid in alignment of the sample container on a particular shelf and/or to provide easy access to the sample container by the sample handling apparatus. In one embodiment, a shelf can include a first and second angled surface, where the first and second angled surface aligns the sample container in the shelf. For example, the first and second angled surface can be angled, tapered or rounded toward the internal space of the shelf to guide the sample container into the interior of the shelf. In another embodiment, a shelf includes a first and second section. The first section is proximal to the central interior of the housing and the second section, which is contiguous to the first section, is proximal to the outer interior of the housing. The second section is optionally smaller than the first section and typically smaller than the sample container, thereby allowing easy access of the sample handling apparatus, e.g., grippers, to grasp the sample container.

The incubation device typically includes a plurality of shelves in which each member of the plurality of shelves is capable of aligning with a different member of the plurality of doors. At least some members of the plurality of shelves can be vertically aligned relative to one another in at least one vertical column, or the shelves can be offset from each other so that they are not aligned vertically. The vertical column optionally includes between, e.g., about two and about 50 or more shelves, about three and about 50 or more shelves, about three and about 40 or more shelves, about three and about 30 or more shelves. In preferred embodiments, the incubation device includes a plurality of vertical columns, which vertical columns are operably connected to a rotatable support disposed in the housing. The plurality of vertical columns optionally includes between, e.g., about two and about 50 or more members, about four and about 50 or more members, about three and about 40 or more members, about three and about 30 or more members. In addition, the device can includes a controller that controls rotation of the rotatable support, e.g., about an X-axis.

Components of the incubation device can also include sensors. For example, a shelf can include a sensor, which can be used for alignment with a door and/or alignment of a sample container in or out of the shelf. In one embodiment, a sensor located on the sample handling apparatus and/or the door and/or shelf can provide a signal to the incubation device to open a particular door or close a particular door. A sensor can also signal correct alignment of the shelf with a particular door. Sensors include optical sensors, photoelectric sensors, infrared sensors, position sensors, laser distance sensors, magnetic sensors and the like.

A computer system having one or more data input source, data storage location, and data output device is optionally a feature of the invention. Data input sources can include, e.g., a bar code reader, an operator input device or other devices transmitting internal housing condition(s) data to the computer. A shelf database in the data storage location is a feature of the invention. Data output devices, e.g., digital readouts or computer monitors, of the invention can display, e.g., sample container information related to a particular shelf, internal conditions, and/or the like.

In certain embodiments, the computer system has a shelf database containing shelf and/or sample container information such as, e.g., whether or not a particular shelf is occupied, location of the shelf, alignment with a particular door, and the like. If a shelf is occupied or will be occupied by a sample container, sample container information can include, e.g., sample container types, sample container creation dates, sample container locations, cell types for each well and volumes for each well, library names, sub-group descriptions, mother/daughter sample container designations, and the like.

For example, the location of any sample container can be uniquely identified, e.g., according to the shelf location. A computer system shelf database can, e.g., track the location of all sample containers and can be updated in near real time with each movement of the sample container through an opening to or from a shelf. For example, the shelves can have, e.g., bar-coded, labels at each shelf to identify sample container locations. Commands can be transmitted from the computer to movement of the carrousel to align the desired shelf with a door. The database can include a consistently updated shelf history and/or sample container history with, e.g., sample container removal or placement dates in the incubation device, sample container activity dates, volumes removed per sample and volumes remaining per sample.

In one embodiment, the invention provides an incubation device that includes (a) a housing comprising a plurality of self-closing doors, which doors close at least one opening disposed through a surface of the housing, wherein the doors are vertically aligned relative to one another in at least one vertical door column; (b) a rotatable support disposed within the housing, which support comprises a plurality of vertical shelf columns, wherein each vertical shelf column comprises a plurality of shelves that are vertically aligned relative to one another, wherein each member of the plurality shelves in a selected vertical shelf column is capable of aligning with a different member of the plurality of self-closing doors in the vertical door column; (c) a sample container handling apparatus disposed external to the housing, which handling apparatus is capable of moving at least one sample container through the opening to or from selected shelves in the plurality of vertical shelf columns; (d) a door hold-open mechanism that comprises a member to which is attached a plurality of prongs, wherein the member is positioned such that one prong is adjacent to each of at least two doors in the vertical column of doors, wherein movement of the door hold-open mechanism in a direction parallel to a longitudinal axis of the vertical column of doors results in a prong contacting any door that is at least partially open, thereby holding open the door that is at least partially open; and, (e) a controller operably connected to the housing, which controller controls one or more internal housing conditions.

BRIEF DESCRIPTION OF THE DRAWINGS

The nature, goals, and advantages of the invention will become more apparent to those skilled in the art after considering the following detailed description when read in connection with the accompanying drawings in which like reference numbers identify like components throughout the drawings. It will be understood that some or all of the figures may be schematic representations for purposes of illustration and do not necessarily depict the actual relative sizes or locations of the elements shown.

FIG. 4A schematically depicts a front view of one embodiment of the incubation device of the invention.

FIG. 4B schematically depicts a top view of one embodiment of the incubation device of the invention.

FIG. 8A schematically depicts a side cutaway view of a vertical column of shelves according to one embodiment of the invention.

FIG. 8B schematically depicts a front cutaway view of a vertical column of shelves according to one embodiment of the invention.

FIG. 8C schematically depicts a top cutaway view of one embodiment of a shelf of the invention.

FIG. 8D schematically depicts a bottom cutaway view of one embodiment of a shelf of the invention.

DETAILED DESCRIPTION

Definitions

Before describing the invention in detail, it is to be understood that this invention is not limited to particular devices or systems, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which the terminology will be used in accordance with the definitions set out below.

The term "vertical" refers to a plane that is approximately perpendicular to a plane of a horizontal or supporting surface.

Incubation Devices

Incubation devices of the invention include a housing with a plurality of doors, e.g., at least two or more doors, typically located in, e.g., a vertical panel located on a side, e.g., front, of the incubator. Typically, a sample handling apparatus located outside the incubator is used to open individual doors located in the access panel as it loads or unloads sample containers into or out of the incubator. This reduces the air exchange between the external environment and the internal environment of the incubation device along with limiting the moving parts within the interior of the incubation device. As a result, the incubation devices of the invention provide a controlled environment for maintaining parameters, such as humidity, temperature, gas conditions (e.g., $CO_2$, $N_2$, or other gas levels).

Figures 1A, 1B:
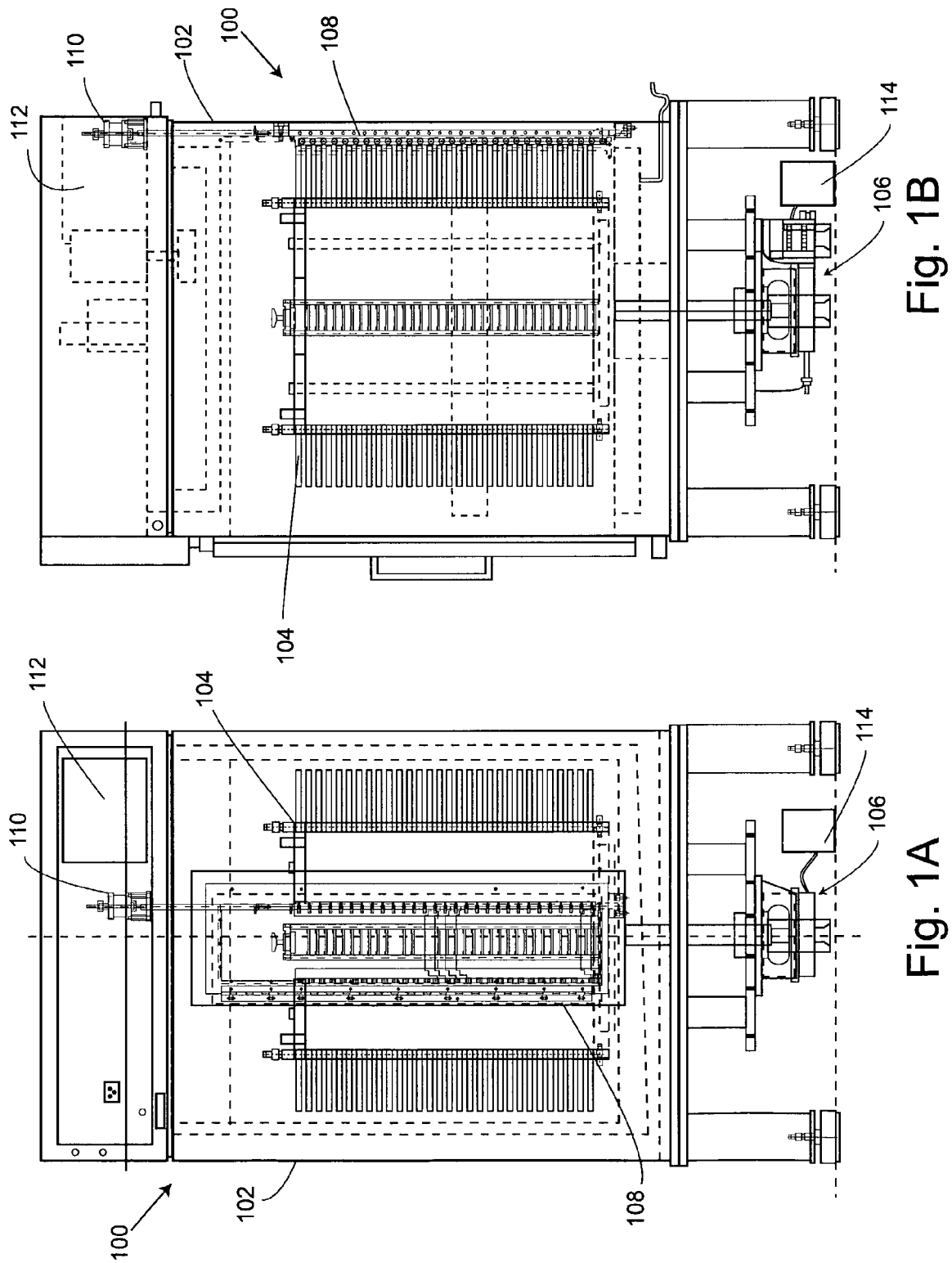
FIG. 1A schematically depicts a front cutaway view of one embodiment of the incubation device of the invention.
FIG. 1B schematically depicts a side cutaway view of one embodiment of the incubation device of the invention.

An incubation device of the invention is illustrated schematically in FIG. 1. FIG. 1A schematically depicts a front cutaway view of one embodiment of incubation device 100. As shown, incubation device 100 includes housing 102 having carrousel with vertical columns of shelves 104 disposed in housing 102. External motor 106 is operably connected to carrousel 104 to rotate selected vertical columns of carrousel 104 into alignment with vertical column of doors 108. Typically, controller 114 controls rotation of carrousel 104. Incubation device 100 also includes controller 112, which controls one or more internal housing conditions. FIG. 1A also schematically illustrates door hold-open mechanism 110 that includes a member (e.g., a rod, a column, a pole, a slat, a bar and the like) having a plurality of prongs (or a series of pins) for holding accessed doors of vertical column of doors 108 open, as described herein. Although not shown, the device also typically includes a sample container handling apparatus (e.g., a robot having a robotic armature, etc.) for inserting and removing sample containers into and out of housing 102. FIG. 1B schematically depicts incubation device 100 from a side cutaway view.

Figure 2B:
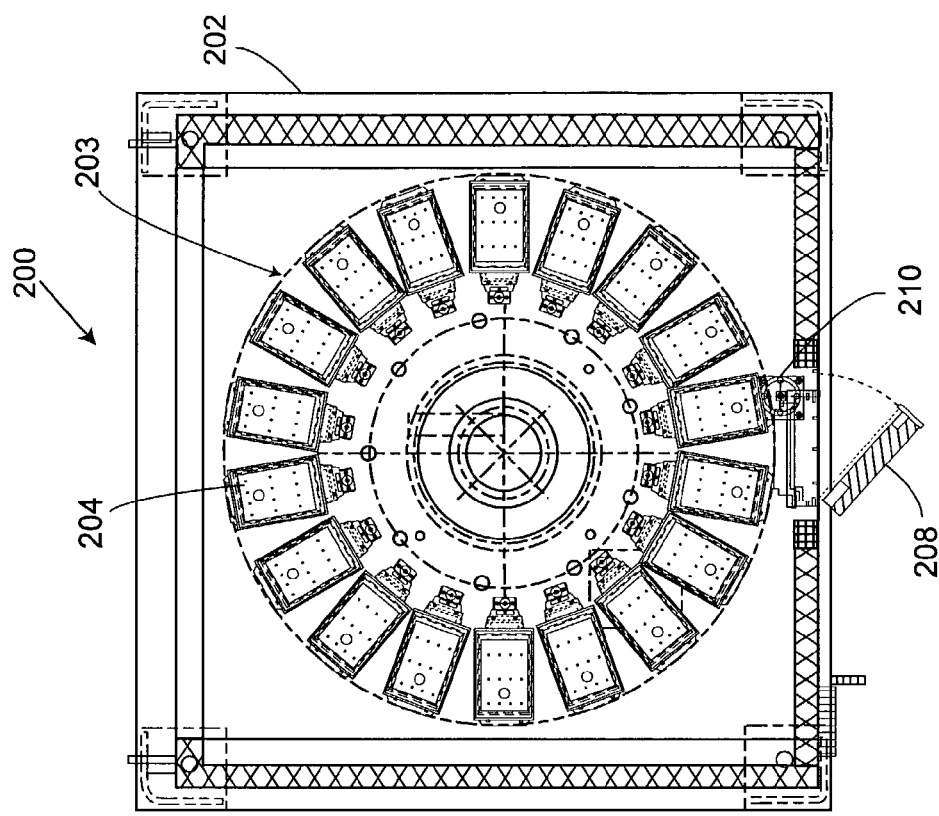
FIG. 2B schematically depicts a bottom cutaway view of one embodiment of the incubation device of the invention.
Figure 2A:
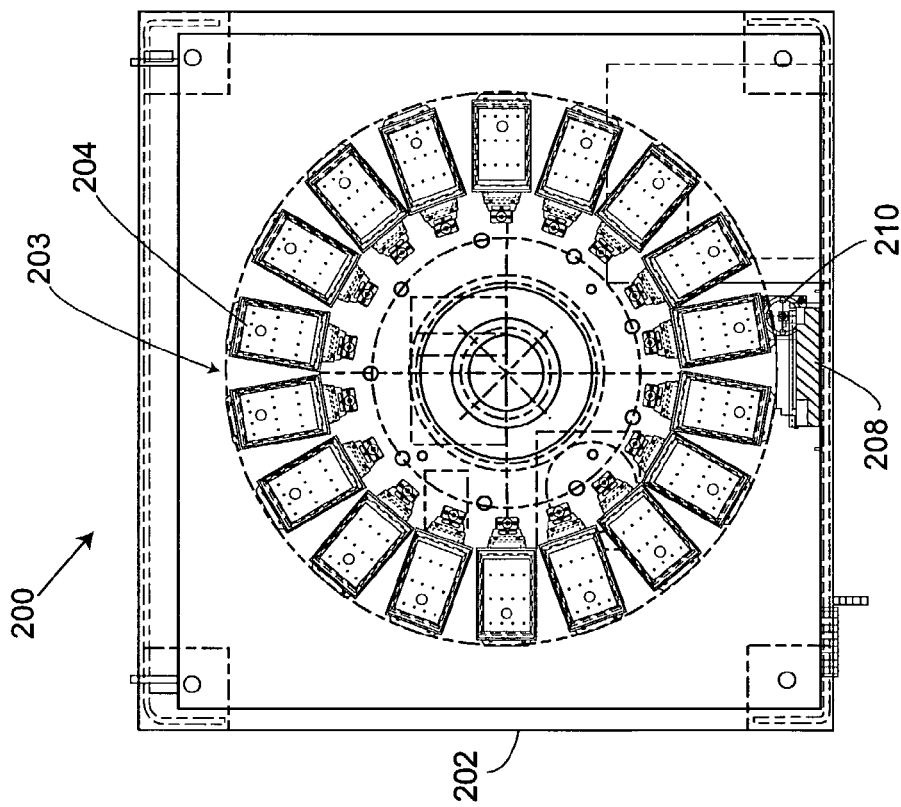
FIG. 2A schematically depicts a top cutaway view of one embodiment of the incubation device of the invention.

A rotating vertical carrousel with multiple columns (commonly referred to as "hotels") and multiple shelves is located inside the incubator. FIG. 2A schematically depicts a top cutaway view of one embodiment of incubation device 200, while FIG. 2B schematically depicts a bottom cutaway view of incubation device 200. Incubation device 200 includes carrousel 203 with a plurality of shelves 204 disposed in housing 202. An external motor is operably connected to carrousel 203 to rotate selected vertical columns of carrousel 203 (e.g., about an X-axis) into alignment with vertical column of doors 208. The "X-axis" refers to an axis in a three-dimensional rectangular coordinate system that is substantially parallel to a horizontal plane and approximately perpendicular to both the y- and z-axes. The incubation device also includes door hold-open mechanism 210 that includes a member (e.g., a rod, a column, a pole, a slat, a bar and the like) having a plurality of prongs (or a series of pins) for holding accessed doors of vertical column of doors 208 open. In one embodiment, vertical column of doors 208 is hinged to housing 202, which provides the ability to open or close vertical column of doors 208. FIGS.

2A and 2B depicts vertical column of doors 208 in an open position, where FIG. 2B also depicts the movement of vertical column of doors 208.

Figure 3:
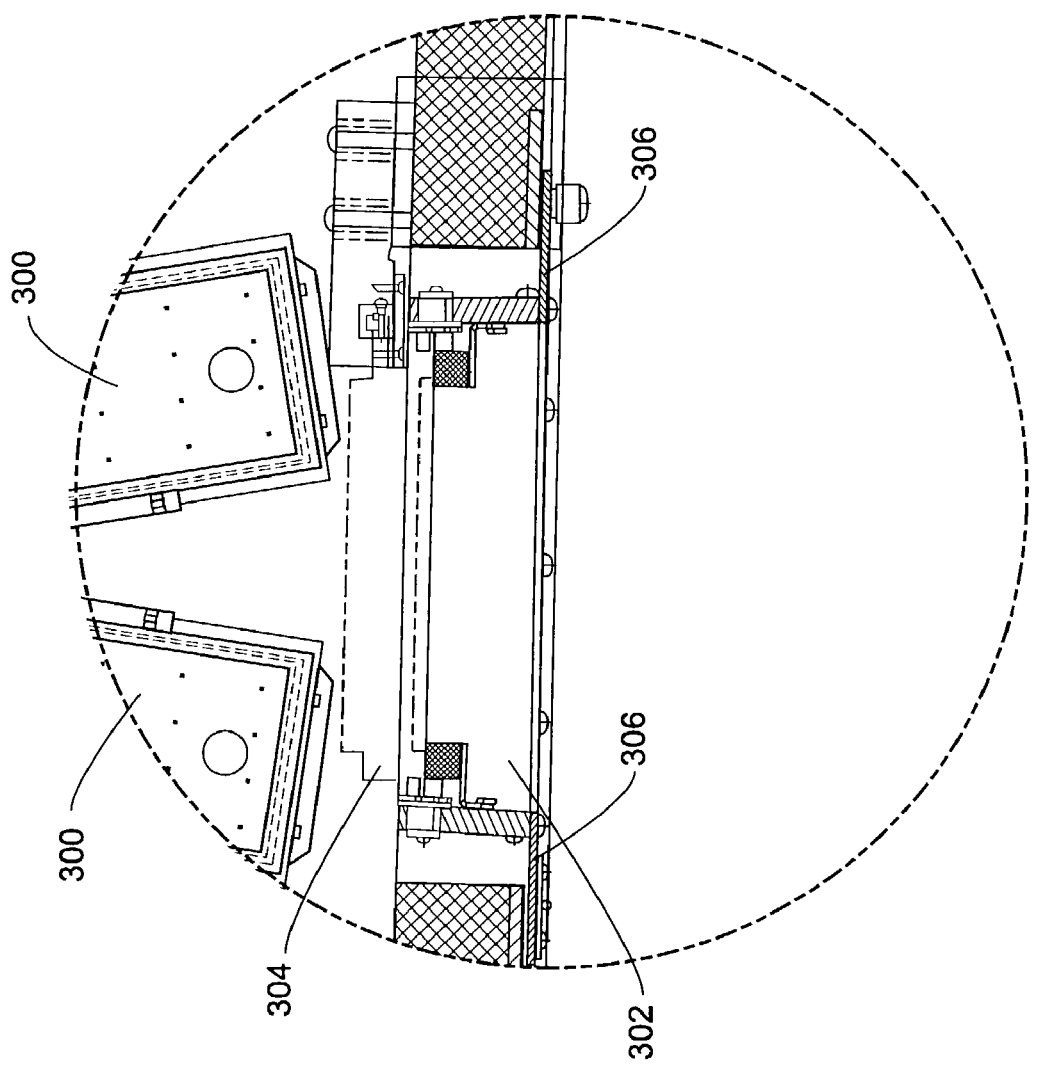
FIG. 3 schematically depicts an isolated top cutaway view of vertical columns of shelves disposed proximal to a vertical column of doors according to one embodiment of the invention.

FIG. 3 schematically depicts an isolated top cutaway view of vertical columns of shelves 300 disposed proximal to vertical column of doors 302. As shown, door 304 is depicted open to show the orientation relative to vertical columns of shelves 300. Rotation (e.g., about an X-axis) of the carrousel aligns one of the shelves 300 with door 304, so that the sample handling apparatus, e.g., robotic armature, can place a sample container on the shelf, or remove such items from the shelf. Typically, vertical column of doors 302 is disposed within a vertical access panel, which optionally includes gasket 306.

Incubation devices of the invention can include a vertical access panel, which is located on a side, e.g., the front, of the incubator. In one embodiment, the access panel is hinged to one side of the incubator. An open access panel provides access to a plurality of shelves in a carrousel and the interior compartment of the incubation device. Optionally, the access panel includes a gasket to seal the interior environment of the incubation device from the exterior environment and a lock or latch to maintain the access panel in a closed position when desired.

FIG. 4A schematically depicts a front view of one embodiment of the incubation device 400. As shown, access panel 402 is disposed in a surface of device housing 404. Access panel 402 includes vertical column of doors 406 and is attached to device housing 404 by hinges 408. Although hinges 408 are depicted on one side of access panel 402, hinges 408 can be placed on any one side of access panel 402. Access panel 402 optionally includes lock 412 or a latch. A portion of door hold-open mechanism 410 is also illustrated. FIG. 4B schematically depicts a top view of one embodiment of the incubation device of the invention.

In another embodiment, the access panel is disposed on the surface of an additional door (e.g., a maintenance door) of the housing. Alternatively, the access panel can be disposed on the on one side surface of the housing and an additional door can be disposed on a different side of the housing. The additional door optionally includes a gasket to seal the interior environment of the incubation device from the external environment and a lock or latch to maintain the door in a closed position when desired.

Figure 5B:
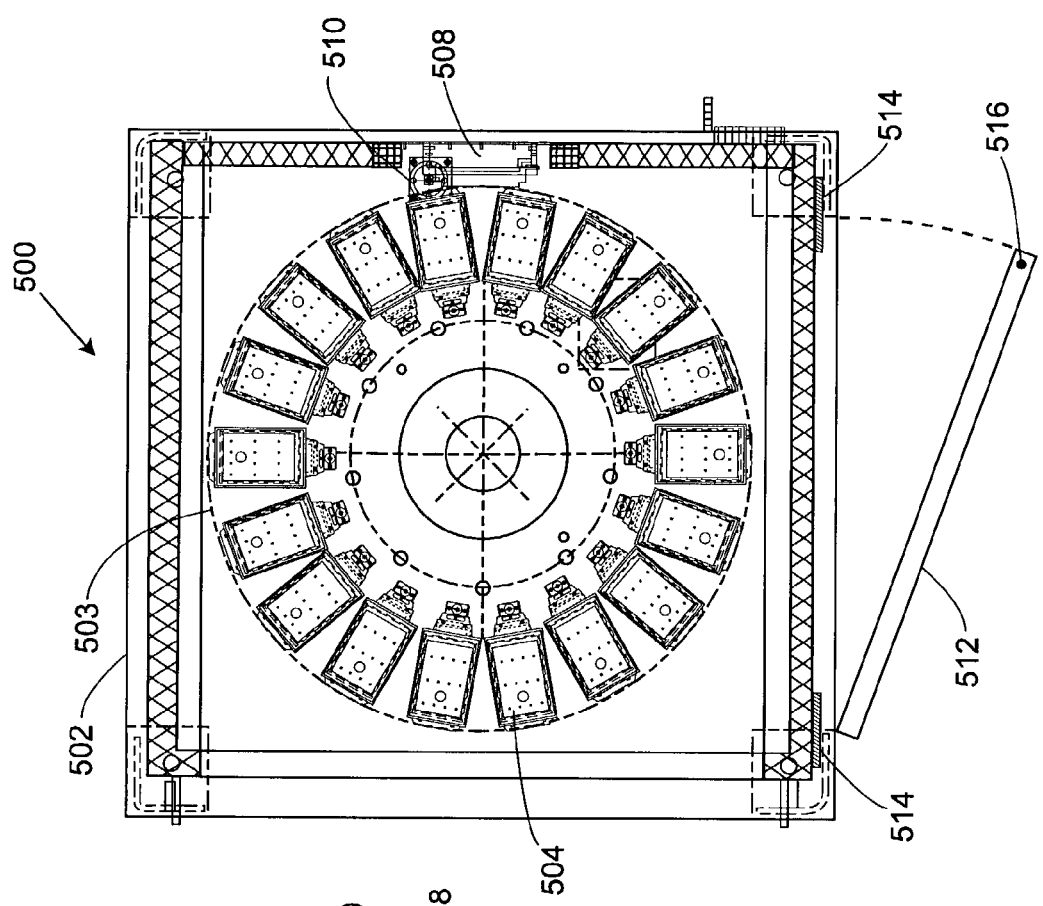
FIG. 5B schematically depicts a bottom cutaway view of one embodiment of the incubation device of the invention.
Figure 5A:
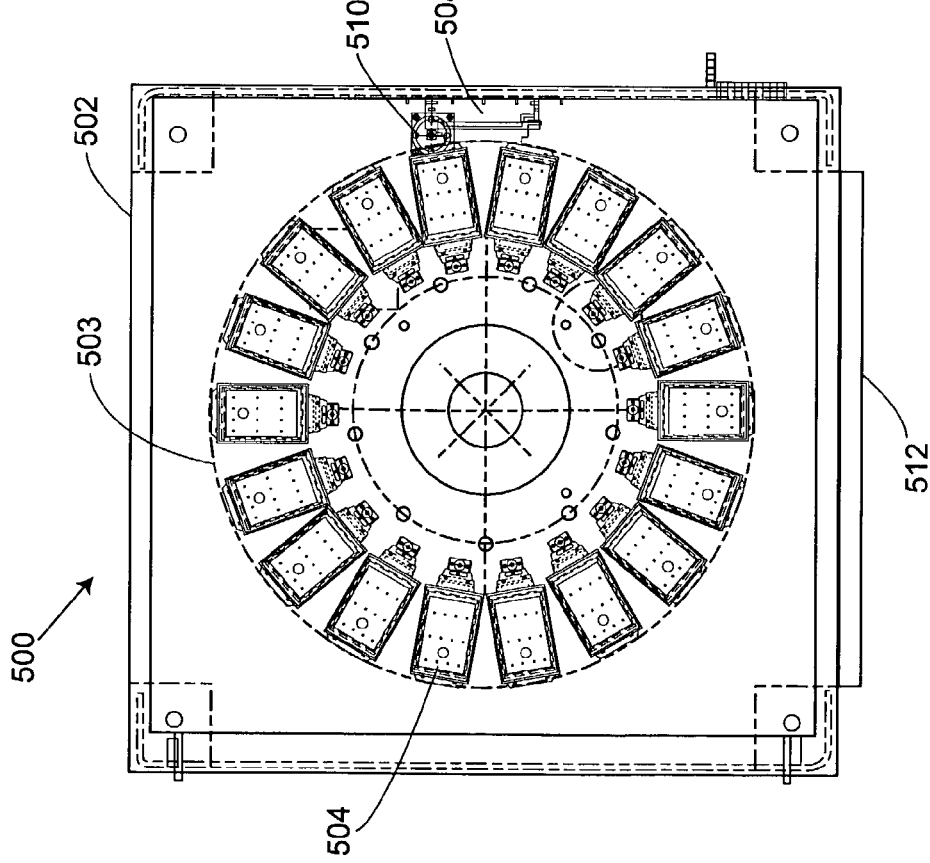
FIG. 5A schematically depicts a top cutaway view of one embodiment of the incubation device of the invention.

FIGS. 5A and 5B schematically depicts one embodiment of the incubation device 500. FIG. 5A depicts a top cutaway view and FIG. 5B depicts a bottom cutaway view of incubation device 500. Housing 502 includes vertical column of doors 508, an additional door (depicted here as maintenance door 512), carrousel 503 with a plurality of shelves 504 disposed with in housing 502. Incubation device 500 also includes door hold-open mechanism 510 that includes a member (e.g., a rod, a column, a pole, a slat, a bar and the like) having a plurality of prongs (or a series of pins) for holding accessed doors of vertical column of doors 508 open. Internal access to housing 502 is accessible via vertical column of doors 508 and/or maintenance door 512. For example, carrousel 503 can be removed or placed in housing 502 via maintenance door 512. Internal access to housing 502 can also be used to clean interior of housing 502. FIG. 5B depicts (an open) maintenance door 512 hinged on one side of housing 502, although maintenance door 512 can be hinged at other side of housing 502. Maintenance door 512 also optionally includes gasket 514 and/or lock 516 or a latch.

The access panel is made up of individual doors that open and provide access to a single sample container in the incubator. The pitch or spacing of the doors is at about the same pitch as the storage shelves on a vertical carrousel disposed in the device housing. There is typically one door for every shelf in the hotel. As a carrousel rotates, different shelves present themselves in front of the door panel.

Figures 6A, 6B, 6C:
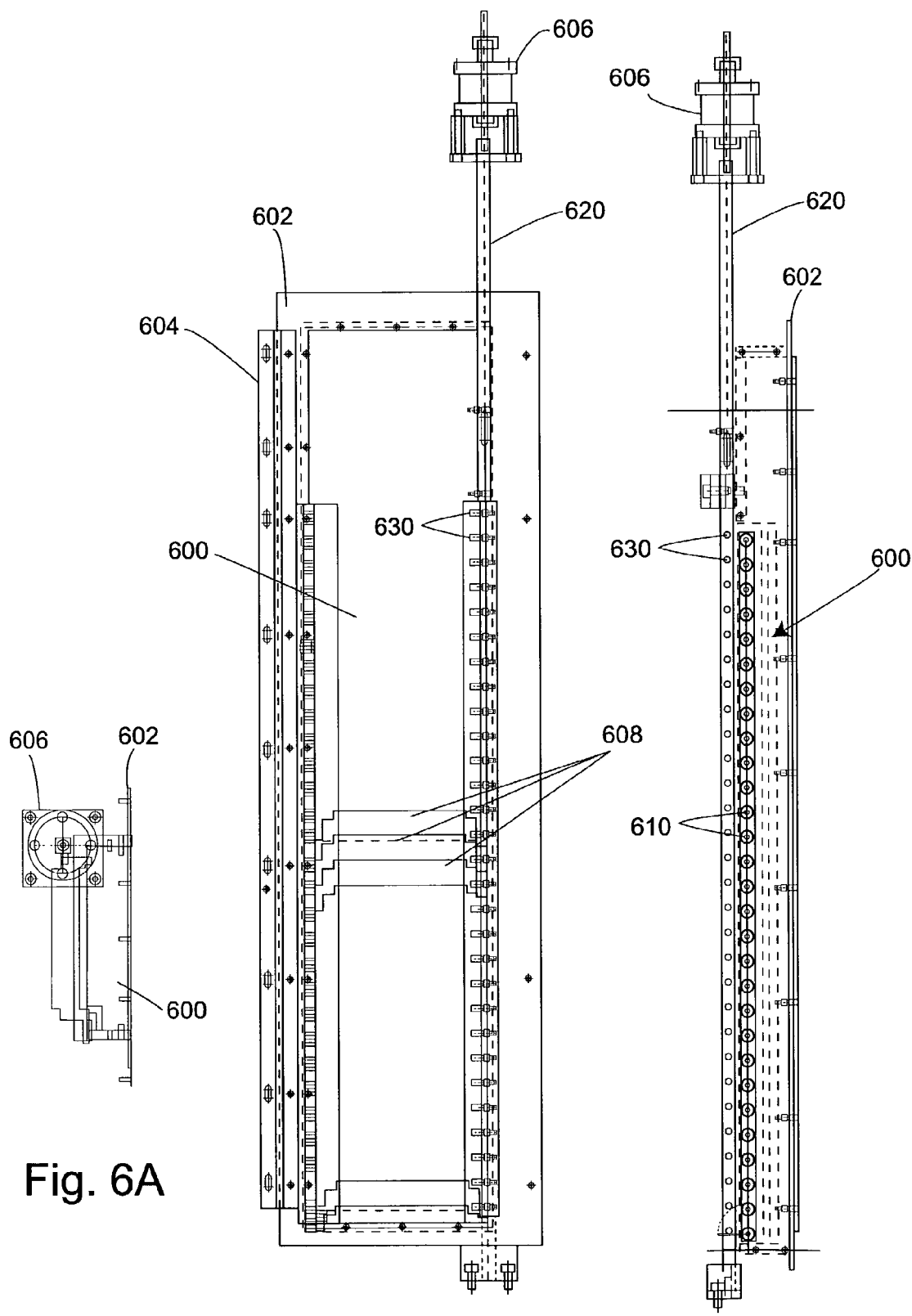
FIG. 6A schematically depicts a top cutaway view of a vertical column of doors according to one embodiment of the invention.
FIG. 6B schematically depicts a front cutaway view of a vertical column of doors according to one embodiment of the invention.
FIG. 6C schematically depicts a side cutaway view of a vertical column of doors according to one embodiment of the invention.

Each door optionally uses a restraining mechanism, e.g., spring mechanism, to keep it shut (e.g., similar to the mechanism on a VCR, automotive cassette player, etc.). FIG. 6A schematically depicts a top cutaway view of vertical column of doors 600 disposed in incubation device access panel 602. FIG. 6B schematically depicts a front cutaway view of vertical column of doors 600. Incubation device access panel 602 is typically attached to an incubation device (not shown) by hinge 604, which affords access to the interior of a device housing by opening access panel 602. As also shown, a door hold-open or restraining mechanism is disposed relative to vertical column of doors 600 to hold doors open, e.g., when aligned shelves are being accessed by a sample handling apparatus, e.g., a gripper, e.g., of a robotic armature. Only three doors 608 are illustrated in FIG. 6B. FIG. 6C schematically depicts a side cutaway view of vertical column of doors 600. As shown, restraining mechanisms 610 (shown in FIG. 6C as springs) close individual doors in the absence of an applied opposing force, such as an entering gripper of a robotic armature.

The door hold-open mechanism can include actuator 606 which moves member 620 back and forth in a direction parallel to a longitudinal axis of the vertical column of doors 600 (FIGS. 6B and 6C). The actuator is shown positioned atop the sample chamber of the incubator (410 in FIG. 4A), but other locations are also suitable. Typically, to member 620 is attached one prong 630 for each door in the vertical column of doors. The prongs 630 are positioned such that such that when a door is partially opened by, for example, a robotic gripper, and member 620 is moved downward (for doors hinged at the bottom), a prong will contact the partially open door and will further open the door and retain the door in an open position. For doors that are hinged at the top, an upward movement of member 620 will result in a prong contacting any partially opened door, thereby further opening the door and retaining the door in the open position. If two or more doors are opened simultaneously (e.g., by two or more robotic grippers accessing the incubator), the single hold-open mechanism can hold open all of the doors due to the presence of a prong adjacent to each of the partially opened doors. The hold-open mechanism of the invention thus requires only a single moving part yet functions to hold open any of the doors in the vertical column of doors.

Figure 7:
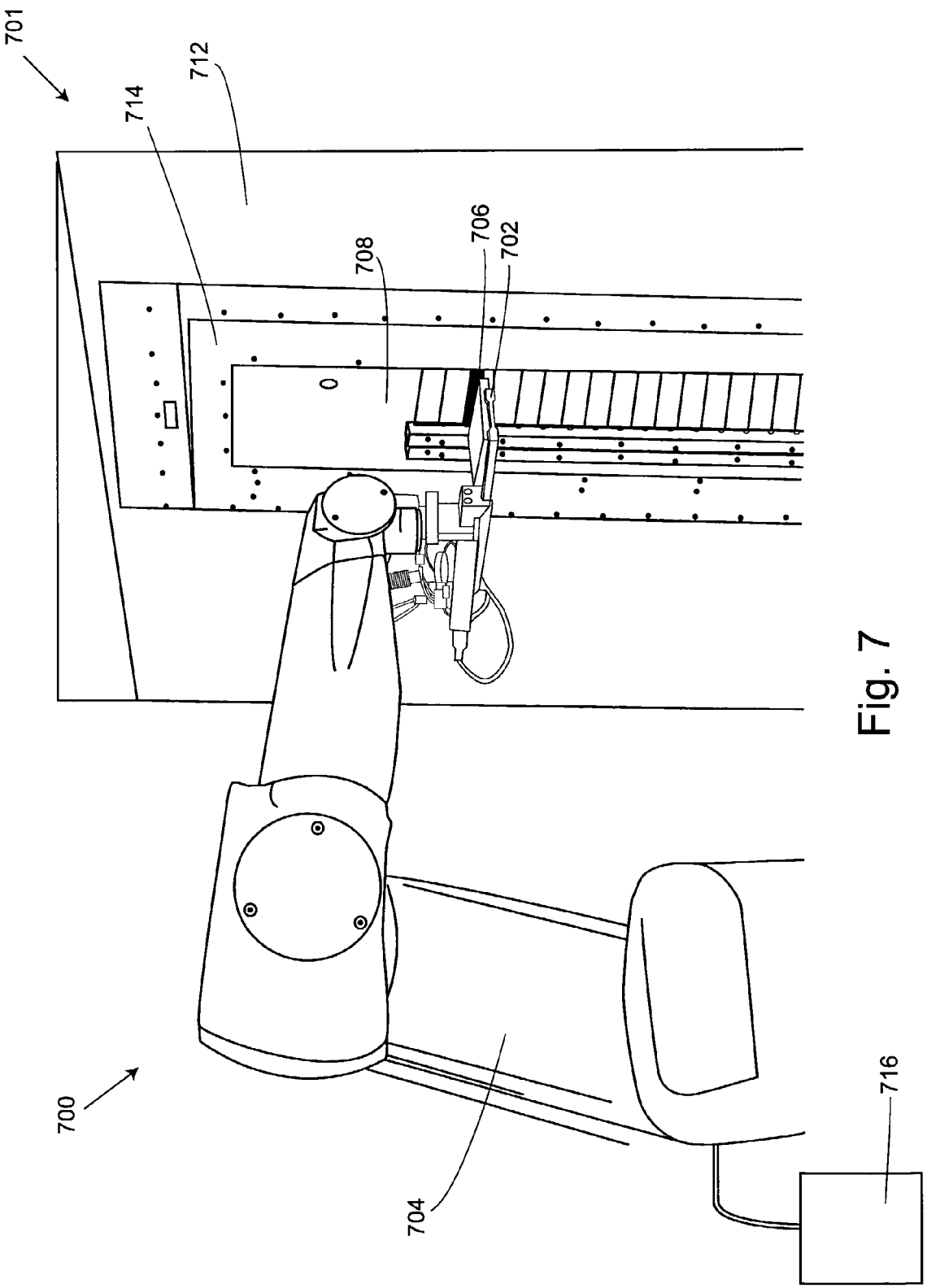
FIG. 7 schematically depicts a gripper of a robotic armature interfacing with a door in a vertical column of doors of an incubation device in one embodiment of the invention.

Individual actuators are not needed to open doors because a sample handling apparatus, e.g., robotic armature, typically provides mechanical actuation to open selected doors. Thus, the incubator need not have any internal mechanism for opening the doors in the vertical column of doors. Since only one relatively small door is open at a time, air exchange between the incubation device and the outside atmosphere is reduced. FIG. 7 depicts an embodiment of the invention, which includes sample handling apparatus 700, e.g., a robot, located outside incubator 701 used to open individual doors 706 on vertical access panel 714. It loads or unloads sample containers into or out of incubator 701. FIG. 7 schematically depicts gripper 702 of robotic armature 704 interfacing with door 706 in vertical column 708 of doors 706 of housing 712 in one embodiment of the invention. In one aspect, sample handling apparatus 700 (illustrated here as a robotic armature) includes logical device 716 for controlling robotic armature.

For example, when a sample handling apparatus, e.g., a robotic armature, requires access to a sample container behind a particular door, the sample handling apparatus contacts the door with, e.g., a gripper, and pushes it open as the gripper moves forward. The force of the sample handling apparatus overcomes the force of the spring trying to keep the door closed. Once the door is at least partially open (e.g., about 70° or about 65°, about 60°, or about 55° from vertical), a door hold-open mechanism further opens the door and holds the door open so that the sample handling apparatus grippers no longer contact the door. For example, in some embodiments the door hold-open mechanism opens the door about an additional about 20° to about 35°. The sample handling apparatus then grabs the sample container, and removes it from the incubator. Once the gripper and the sample container are clear of the door, the door hold-open mechanism is released and the spring forces the single door closed. The internal environment of the incubator is exposed to the external environment for only a short time, which reduces air transfer between the two environments. The size of the door is preferably just large enough to provide access for a single sample container, and the gripper.

Placing the sample container into the incubator is very similar to the above-described process. However, instead of using the gripper to initially contact the door, the sample container disposed in the gripper contacts the door. Again, once the door is pushed open by the sample container (e.g., about 70°, about 65°, about 60°, or about 55° from vertical), the door hold-open mechanism further opens the door and holds the door open so that the sample container no longer contacts the door. When the door is almost fully open (e.g., greater than about 75°, greater than about 85°, greater than about 90°, greater than about 95° or more), neither the robot gripper nor the sample container are in contact with the door. The robot then places, e.g., the sample container on the shelf, unclamps from the sample container, and leaves the sample container in the incubator. Once the gripper is clear of the door, the door hold-open mechanism is released and the spring forces the door closed.

Thus, moving parts within the incubation device are typically limited to the carrousel and a single restraint or hold-open mechanism that holds open doors that are opened. Reliability and serviceability are dramatically improved because all the mechanical parts for opening the doors are part of the sample handling device and external to the incubation device. Should mechanical components fail, repairs are readily made without disturbing the internal environment within the incubator.

Individual shelves can include a number of embodiments to aid in accessing a sample container from a shelf and/or in placing and aligning the sample container on a particular shelf. For example, a section of the shelf, e.g., a second section, is smaller than a first section and typically smaller than a sample container, which provides an area on the sample container where the sample handling apparatus is able to freely grip the sample container without contacting the shelf. Sides of the shelves can also be angled, tapered or rounded to align the sample container on a particular shelf.

FIG. 8A schematically depicts a cutaway side view of one embodiment of vertical column of doors 800 disposed in incubation device. FIG. 8B schematically depicts a front cutaway view of the vertical column of shelves 804 with sides of shelves 804 including first angled surface 806 and second angled surface 808. FIG. 8C schematically depicts a top cutaway view of one embodiment of shelf 804, which includes first section 810 and second section 812. FIG. 8D schematically depicts a bottom cutaway view of one embodiment of shelf 804, which includes first section 810 and second section 812. One embodiment of shelf 804 includes identification label 816. Optionally, shelf 804 includes sensor 818. Identification label 816 and sensor 818 can also be located in a variety of embodiments on shelf 804.

Figure 8E:
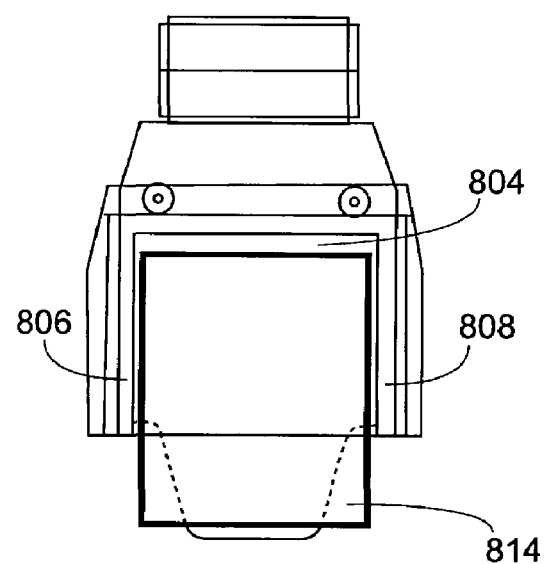
FIG. 8E schematically depicts a top cutaway view of one embodiment of a shelf of the invention with a sample container.
Figure 8F:
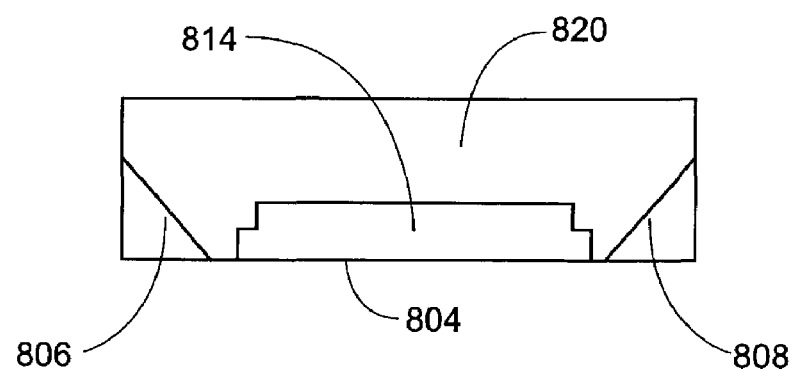
FIG. 8F schematically depicts a front cutaway view of one embodiment of a shelf of the invention.
Figure 8G:
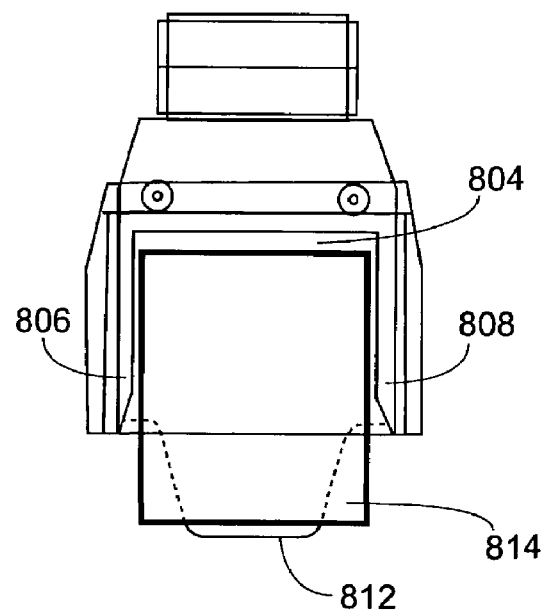
FIG. 8G schematically depicts a top cutaway view of a shelf according to one embodiment of the invention.

FIG. 8E schematically depicts shelf 804 with first angled surface 806 and second angled surface 808 holding sample container 814. In one embodiment, shelf 804 includes first angled surface 806 and second angled surface 808, which aid in aligning sample container 814 on the shelf 804. In one aspect, as shown in FIG. 8F first angled surface 806 and second angled surface 808 are tapered toward interior 820 of shelf 804. FIG. 8G schematically depicts another embodiment of the invention, where first angled surface 806 and second angled surface 808 are tapered toward second section 812. When a sample container is placed on the shelf by, for example, a robotic gripper, the angled surfaces position the sample container in a precise desired position. Although shown in FIG. 8F with a gap between the bottom inward-facing portion of the angled surfaces and the sample container, in some embodiments the angled surfaces contact the sample container with little or no excess clearance, thereby providing for precise positioning. The angled surfaces are shown as angled, but can also have other shapes (e.g., tapered, rounded) that will provide for precise positioning of a sample container on the shelf.

Sample containers that can be used in the incubation devices of the invention include a number of objects. For example, sample containers include microwell plates (e.g., 6-well, 12-well, 24-well, 48-well, 96-well, 384-well, and 1536-well microtiter plates), other labware and the like. Other exemplary sample containers include, e.g., reaction blocks, reaction block carriers, petri dishes, test tubes, test tube racks, vials, crucibles, reaction vessels or flasks, hazardous material containers, medical devices or components, trays, etc. Reaction blocks and reaction block carriers are described in greater detail in, e.g., U.S. Ser. No. 09/947,236, entitled "Parallel Reaction Devices," filed Sep. 5, 2001 by Micklash et al., and U.S. Ser. No. 60/351,821, entitled "Devices, Systems, and Methods of Manifolding Materials," filed Jan. 25, 2002 by Micklash et al., the disclosures of which are incorporated by reference in their entirety for all purpose. Microwell plates that are placed in the incubator can be covered by, for example, specimen plate lids such as those that are described in International Patent Application WO 01/85550.

In certain embodiments, sensors are a feature of the invention. In one embodiment, a shelf includes a sensor for alignment with a door, for interaction with a sample handling apparatus, etc. In another embodiment, sensors located on a door, and/or the sample handling apparatus, and/or shelf can be used to signal the incubation device to open a particular door or close a particular door. Examples of sensors include optical sensors, photoelectric sensors, infrared sensors, position sensors, laser distance sensors, magnetic sensors and the like.

The incubation devices, or components thereof, of the invention are typically operably connected to one or more logic devices, such as computers or other information appliances. A logic device generally includes system software that directs, e.g., the gripper of the robotic armature to grasp selected sample containers, the movement of the robotic armature mass relative to the incubation device, or the like. For example, device components are optionally coupled to an appropriately programmed processor or computer which functions to instruct the operation of these instruments in accordance with preprogrammed or user input instructions, receive data and information from these instruments, and interpret, manipulate and report this information to the user.

Figure 9:
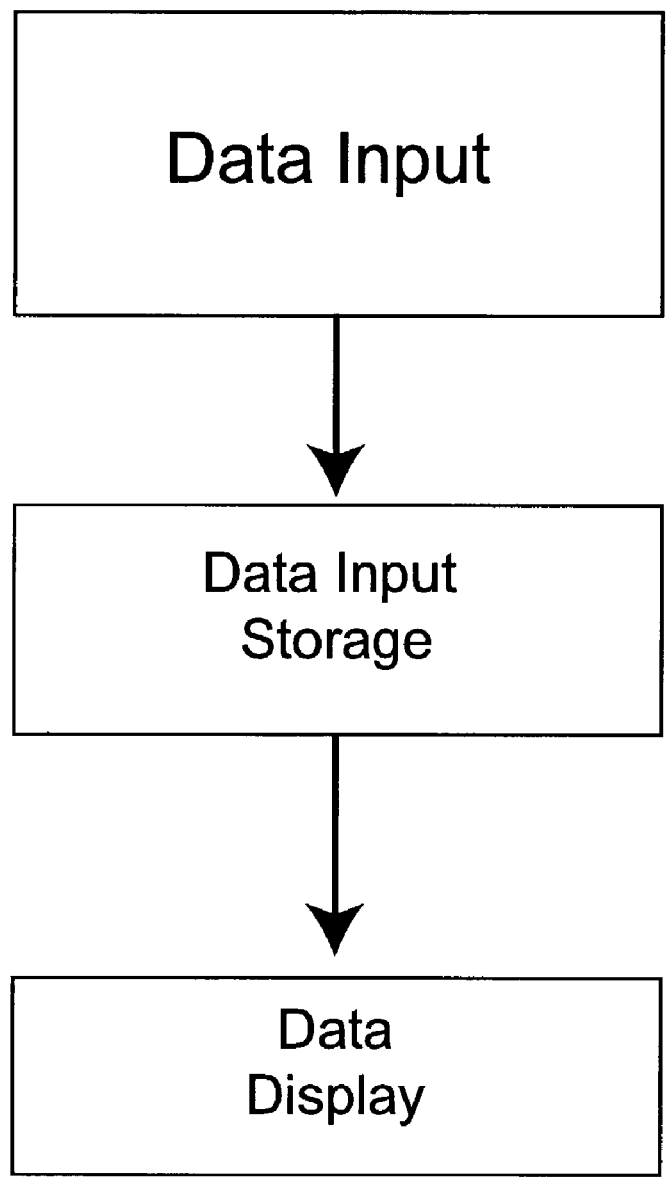
FIG. 9 is a block diagram illustrating one embodiment of a computer system of an incubation device.
Figure 10:
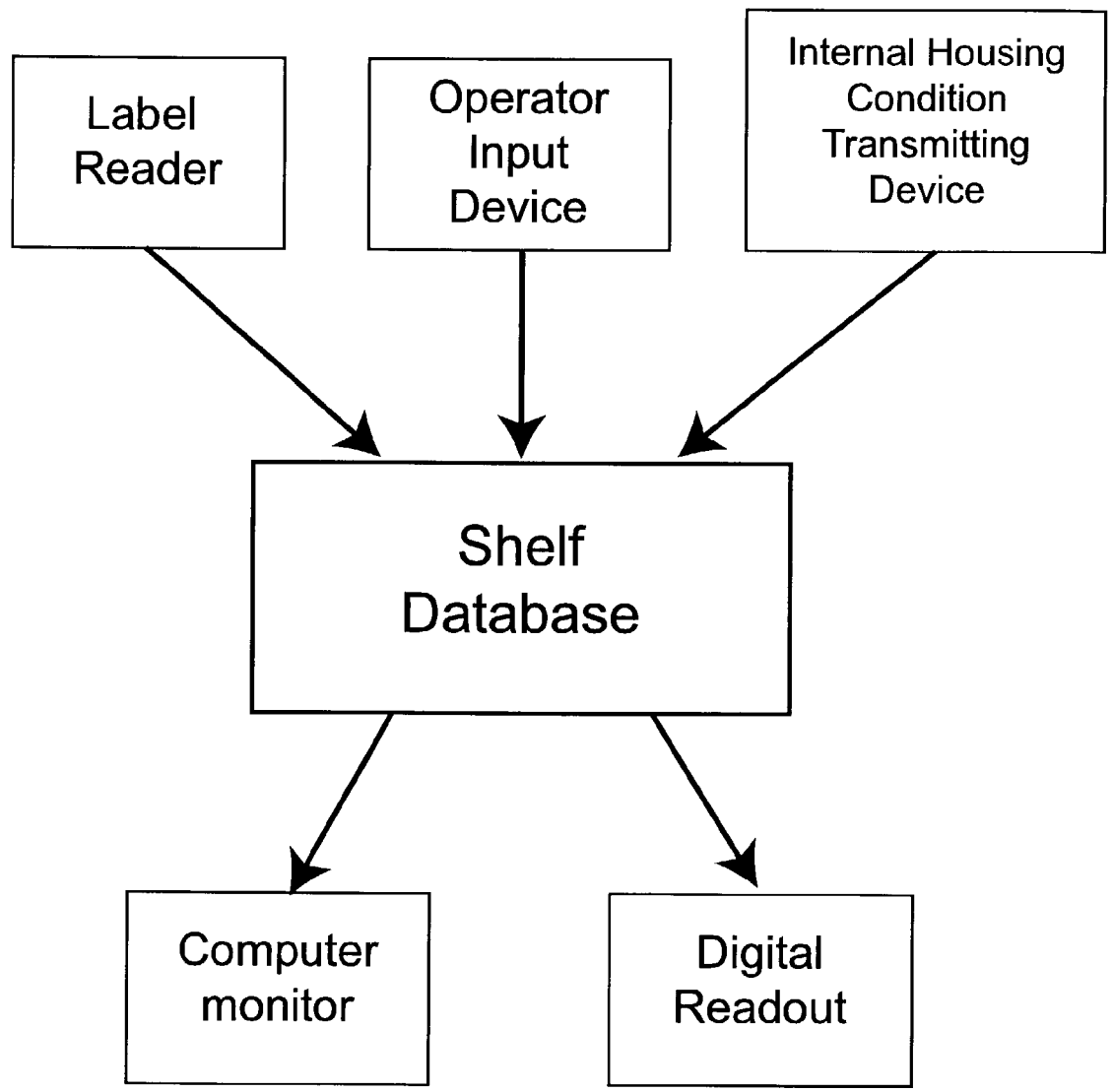
FIG. 10 is a block diagram illustrating one embodiment of a computer system of an incubation device.

Computer systems in the incubation device can play many roles. The computer systems can acquire data, store data and display data relevant to incubation devices of the invention (FIG. 9). One embodiment is diagramed in FIG. 10. The computer systems can provide instructions to operators, direction the operators or even exercise physical control over operator actions.

The computer is optionally, e.g., a PC (Intel x86 or Pentium chip-compatible DOS™, OS2™, WINDOWS™, WINDOWS NT™, WINDOWS95™, WINDOWS98™, LINUX based machine, a MACINTOSH™, Power PC, or a UNIX based (e.g., SUN™ work station) machine) or other commercially common computer which is known to one of skill. Software for performing the operations described herein is optionally easily constructed by one of skill using a standard programming language such as Visual basic, Fortran, Basic, Java, or the like. Any controller or computer optionally includes a monitor which is often a cathode ray tube ("CRT") display, a flat panel display (e.g., active matrix liquid crystal display, liquid crystal display), or others. Computer circuitry is often placed in a box that includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing, e.g., the control of internal housing conditions, the sample handling operations, movement of a particular shelf to a particular door of the incubation device, etc.

Data acquisition by the computer systems of the invention can include maintenance of an accurate sample inventory, movement of sample containers via a sampling handling device, internal housing conditions and the like. For example, when a change is made to a sample container in the incubation device, e.g., insertion of a sample container, movement of a sample container to a new location, removal of a sample container, and the like, the change can be documented in the inventory.

Inventory changes can be updated in the shelf database of the invention through operator input devices such as manual data entry using a computer keyboard. Shelf database information suitable for operator data entry includes, e.g., library names, subgroup descriptions, mother/daughter sample container designations, sample container types, compound structures or cell types, volumes removed per sample, volumes remaining per sample, and the like. Such data can be entered as a large batch of data in spreadsheet form. Alternately, such data can be entered in near real time on the operator's initiative or with computer prompting.

Inventory changes can also be updated to the shelf database to include sample container information by scanning, e.g., of bar code, labels. For example, identification labels, e.g., bar codes and the like, can be placed on the shelves and/or sample containers, which can make identification of sample containers, location of a particular shelf and data acquisition easier and more reliable. Sample container information suitable for scanned data input includes, e.g., sample container creation dates, sample container locations, sample container movement dates, sample container activity dates, and the like. Scanned data is often acquired real time and with high reliability.

Internal housing condition information can be captured by data input sources and transmitted to the computer for storage or output. Such data includes, e.g., temperature, humidity, gas composition, and the like. Instruments acting as data input sources can be simple, e.g., a thermosistor providing direct analog input of an internal housing temperature. More complex data input sources can be computerized instruments, e.g., analytical systems, in digital communication with the computer. Data acquisition can be continuous or intermittent depending on scientific and regulatory requirements. Thresholds, e.g., maximum or minimum temperatures, maximum and minimum humidity levels maximum, minimum gas composition levels and the like, can be established provide an alarm warning an operator of an unsuitable or hazardous condition.

Data acquired by the computer can be stored in databases, e.g., as a record of the past internal housing conditions or to establish the current status of shelves and/or sample containers. In one embodiment of the invention, a shelf database is compiled to reflect the current status of shelves and/or sample containers in the incubation device. The shelf database can include, e.g., status of a shelf (e.g., occupied or not occupied), library names, sub-group descriptions, mother/daughter sample container designations, sample container types, sample container creation dates, sample container locations, compound structures or cell types for each well, volumes for each well, and the like. Stored data can be transmitted to output devices for viewing or analysis.

The computers of the incubation device provide data output useful to, e.g., inform an operator of system conditions, prompt an operator to take actions, supply system documentation, and prevent errors. Data output devices of the invention include, e.g., liquid crystal (LC) displays, computer monitors, printers, and command interface boards connected to, e.g., lights, locks and alarms.

Data output devices can inform an operator of system conditions. For example, a computer monitor or LC can display the internal housing conditions, e.g., temperature, humidity, gas composition and the like. An operator can then respond if degrading conditions indicate a system maintenance problem. The operator can decide to delay additional sample container movement operations until the desired internal housing conditions are met.

Data output consisting of procedural instructions for an operator is also a feature of the invention. The retrieval and storage methods, described herein, provide reliable sample handling and accurate inventories with careful attention to detail by the operator. Computer output of instructions and directions can help to insure proper functioning of the system.

The computer system can transmit commands to take actions ensuring smooth operation of incubation device of the invention. The computer system can be operably coupled, through an interface, to physical actuators, e.g., lights and alarms, to provide certain notice of system requirements to the operator. The computer can actuate alarms to warn of, e.g., open and/or malfunctioning doors, undesirable internal housing conditions, incorrect sample container reloading, and the like.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. An incubation device, comprising:
   (a) a housing that comprises a plurality of doors arranged in at least one vertical column, which doors close at least one opening disposed through a surface of the housing; and
   (b) a door hold-open mechanism disposed parallel to a longitudinal axis of the vertical column of doors, said mechanism comprising a member to which is attached a plurality of prongs, wherein the member is positioned such that one prong is adjacent to each of at least two doors in the vertical column of doors; and
   wherein movement of the door hold-open mechanism in the direction parallel to a longitudinal axis of the vertical column of doors results in a prong contacting any door that is at least partially open, thereby holding open the door that is at least partially open.

2. The incubation device of claim 1, wherein the door hold-open mechanism is moveably coupled to the housing by an actuating device that moves the door hold-open mechanism back and forth in the direction parallel to the longitudinal axis of the column of doors.

3. The incubation device of claim 1, wherein each door is hinged at a bottom edge of the door and downward movement of the door hold-open mechanism results in a prong contacting the door, if the door is at least partially open, and holding the door open until the door hold-open mechanism is moved in an upward direction.

4. The incubation device of claim 1, wherein at least one of the doors comprises a restraining mechanism connected thereto that closes the door closed in the absence of an applied opposing force.

5. The incubation device of claim 4, wherein the restraining mechanism is self-actuating.

6. The incubation device of claim 4, wherein the actuation mechanism comprises at least one spring.

7. The incubation device of claim 1, wherein the doors in the vertical column of doors do not comprise individual actuator mechanisms for opening the doors.

8. The incubation device of claim 1, further comprising at least one movable shelf disposed within the housing, which shelf is capable of aligning with the opening.

9. The incubation device of claim 8, wherein the shelf comprises a first and second angled surface, wherein the first and second angled surfaces align a sample container on the shelf.

10. The incubation device of claim 9, wherein the first and second angled surfaces are angled, tapered or rounded towards an internal space of the shelf.

11. The incubation device of claim 8, wherein the shelf comprises:
   (a) a first section, wherein the first section is proximal to central interior of the housing; and
   (b) a second section, which is contiguous to the first section and proximal to the outer interior of the housing, wherein the second section is smaller than the first section and when the shelf is aligned with the opening the second section allows a handling apparatus to grip the sample container through the opening.

12. The incubation device of claim 8, wherein the shelf comprises an identification label.

13. The incubation device of claim 8, wherein the shelf comprises a sensor.

14. The incubation device of claim 1, further comprising a sample container handling apparatus disposed external to the housing, which handling apparatus is capable of moving at least one sample container through the opening to or from the shelf.

15. The incubation device of claim 14, wherein each of the doors is independently accessible by the sample container handling apparatus.

16. The incubation device of claim 14, wherein the sample container handling apparatus comprises a robotic armature.

17. The incubation device of claim 14, wherein the sample container handling apparatus comprises a gripper configured to grip a sample container.

18. The incubation device of claim 17, wherein the sample container is selected from the group consisting of: a plate, a sample plate, a micro-well plate, a reaction block, a reaction block carrier, a sample holder, a petri dish, a test tube, a test tube rack, a vial, a crucible, a reaction vessel, a reaction flask, and a tray.

19. The incubation device of claim 14, further comprising at least one logic device operably connected at least to the sample container handling apparatus, which logic device comprises one or more logic instructions that direct movement of the sample container handling apparatus.

20. The incubation device of claim 1, further comprising a first controller operably connected to the housing, which first controller controls one or more internal housing conditions.

21. The incubation device of claim 20, wherein the internal housing conditions comprise one or more of: temperature, humidity, or gas composition.

22. The incubation device of claim 1, wherein the vertical column comprises an access panel.

23. The incubation device of claim 22, wherein the access panel is hinged to the housing.

24. The incubation device of claim 23, wherein the access panel comprises a gasket and a lock or latch.

25. The incubation device of claim 22, wherein the access panel is disposed within an additional door in the housing.

26. The incubation device of claim 1, wherein the vertical column of doors comprises between two and 50 doors.

27. The incubation device of claim 1, wherein the incubation device comprises a plurality of shelves, wherein each member of the plurality of shelves is capable of aligning with a different door in the vertical column of doors.

28. The incubation device of claim 27, wherein at least some members of the plurality of shelves are vertically aligned relative to one another in at least one vertical column.

29. The incubation device of claim 28, wherein the vertical column comprises between two and 50 shelves.

30. The incubation device of claim 28, wherein the incubation device comprises a plurality of vertical columns, which vertical columns are operably connected to a rotatable support disposed in the housing.

31. The incubation device of claim 30, wherein the plurality of vertical columns comprises between two and 50 members.

32. The incubation device of claim 30, further comprising a controller that controls rotation of the rotatable support.

33. The incubation device of claim 1, further comprising an additional door that is not present in a vertical column of doors, wherein the additional door allows access to interior of housing.

34. The incubation device of claim 33, wherein the additional door comprises a gasket and a lock or latch.

35. The incubation device of claim 1, further comprising a computer system comprising one or more data input source, a data storage location and a data output device.

36. The incubation device of 35, wherein the one or more data input source is a label reader, an operator input device or internal housing condition transmitting device.

37. The incubation device of claim 35, wherein the data storage location comprises a shelf database.

38. The incubation device of claim 35, wherein the data output device comprises a computer monitor or digital readout.

39. An incubation device, comprising:
  (a) a housing comprising a plurality of self-closing doors, which doors close at least one opening disposed through a surface of the housing, wherein the doors are vertically aligned relative to one another in at least one vertical door column;
  (b) a rotatable support disposed within the housing, which support comprises a plurality of vertical shelf columns, wherein each vertical shelf column comprises a plurality of shelves that are vertically aligned relative to one another, wherein each member of the plurality shelves in a selected vertical shelf column is capable of aligning with a different member of the plurality of self-closing doors in the vertical door column;
  (c) a sample container handling apparatus disposed external to the housing, which handling apparatus is capable of moving at least one sample container through the opening to or from selected shelves in the plurality of vertical shelf columns;
  (d) a door hold-open mechanism disposed parallel to a longitudinal axis of the vertical column of doors, said mechanism comprising a member to which is attached a plurality of prongs, wherein the member is positioned such that one prong is adjacent to each of at least two doors in the vertical column of doors, and wherein movement of the door hold-open mechanism in the direction parallel to a longitudinal axis of the vertical column of doors results in a prong contacting any door that is at least partially open, thereby holding open the door that is at least partially open; and,
  (e) a controller operably connected to the housing, which controller controls one or more internal housing conditions.

* * * * *